US006833464B2

(12) United States Patent
Gabbai et al.

(10) Patent No.: US 6,833,464 B2
(45) Date of Patent: Dec. 21, 2004

(54) CATALYST COMPOSITION, METHOD OF MAKING SAME AND ITS USE IN OLEFIN POLYMERIZATION

(75) Inventors: Francois Gabbai, Brazos County, TX (US); Mani Ganesan, Brazos County, TX (US); Dave S. Pope, Travis County, TX (US); Jimmy D. Brown, Travis County, TX (US); Donald L. Wharry, Travis County, TX (US); Paul K. Hurlburt, Boulder County, TX (US)

(73) Assignee: The Texas A&M University System, College Station, TX (US)

( * ) Notice: Subject to any disclaimer, the term of this patent is extended or adjusted under 35 U.S.C. 154(b) by 26 days.

(21) Appl. No.: 10/437,539

(22) Filed: May 14, 2003

(65) Prior Publication Data

US 2004/0229749 A1 Nov. 18, 2004

(51) Int. Cl.$^7$ .............................. C07F 17/00; B01J 31/00
(52) U.S. Cl. .............................. 556/53; 556/43; 556/46; 556/58; 556/140; 502/103; 502/117; 526/121; 526/162; 526/943
(58) Field of Search .............................. 556/43, 46, 53, 556/58, 140; 526/121, 162, 943; 502/103, 117

(56) References Cited

FOREIGN PATENT DOCUMENTS

| EP | EP 0 919 571 A1 | 2/1999 |
|----|------------------|--------|
| WO | WO 02/42313 A2  | 5/2002 |

OTHER PUBLICATIONS

Scope of Olefin Polymerization Nickel Catalysts, Science's Compass, Science, vol. 288, Jun. 9, 2000—3 pages.
Neutral, Single–Component Nickel (II) Polyolefin Catalysts That Tolerate Heteroatoms, Todd R. Younkin et al., Science, vol. 287, Jan. 21, 2000—3 pages.
Constrained Geometry Chromium Catalysts for Olefin Polymerization, Yuanfeng Liang, et al., Received Sep. 9, 1996, Organometallics 1996, 15, 5284–5286, 1996 American Chemical Society.
The Role of Metallacycles in the Chromium–Catalyzed Trimerization of Ethylene, Rainer Emrich, et al., Received Dec. 12, 1996, Organometallics, vol. 16, No. 8, Apr. 15, 1997, 1997 American Chemical Society, 3 pages.
Paramagnetic (Benzyl) chromium Complexes as Homogeneous Ethylene Polymerization Catalysts, Gautam Bhandari, et al., Received Sep. 16, 1994, Organometallics 1995, 14, 738–745.
Perfluorophenyl Derivatives of the Elements I. Tri(Pentafluorophenyl) Boron, A.G. Massey et al., Received Feb. 14, 1964, Journal of Organometallic Chemistry, 245–250.
Paramagnetic (Benzyl) chronium Complexes, Experimental Section, Organometallics, vol. 14, No. 2, 1995, pp. 743–745.
Understanding alkyl exchange processes in mixtures containing ATE, a fluorinated boron activator and a zirconocene pre–catalyst, Ganesan Mani, Texas A&M University, Jan. 8, 2003.

*Primary Examiner*—Porfirio Nazario-Gonzalez
(74) *Attorney, Agent, or Firm*—C. James Bushman; Browning Bushman P.C.

(57) ABSTRACT

A composition of matter comprising a compound having the general formula:

$$[CpM(Ar_F)Y]_p$$

wherein
Cp is a substituted or unsubstituted cyclopentadienyl ligand or cyclopentadienyl-type bulky ligand characterized by one or more open, acylic or fused ring systems comprised of atoms selected from Groups 13–16 of the Periodic Table of Elements and wherein the ligands can include a heteroatom;
M is a metal selected from Groups 3–9 of the Periodic Table of Elements;
$Ar_F$ is a fluorinated aryl group;
Y is a hydrocarbyl group that can contain a heteroatom; and p is 1 or 2. The invention also contemplates a method of producing the compound and its use in the oligomerization and polymerization of alpha olefins.

15 Claims, 3 Drawing Sheets

CATALYST COMPOSITION, METHOD OF MAKING SAME AND ITS USE IN OLEFIN POLYMERIZATION

FIELD OF THE INVENTION

The present invention relates to metallic complexes as catalysts for the polymerization or oligomerization of olefins such as alpha olefins and, more particularly, to a catalyst composition that is neutral and does not require the use of activators.

BACKGROUND OF THE INVENTION

The prior art is replete with numerous catalysts and catalyst systems for use in polymerizing olefins such as alpha olefins. Typically, these catalysts or catalyst systems are well-defined molecular transition metal complexes that normally require an activator such as Lewis and Bronsted acid activators, whose primary role is to abstract a ligand from the neutral transition metal. The net result is the formation of cationic complexes as the catalytic active species. When a material such as methylalumoxane is used, activation also requires methylation of the metal center to obtain an active catalyst.

More rarely, neutral complexes have been found to be catalytically active in the polymerization of olefins. In this regard, in addition to Group 3 complexes, square planar alkyl nickel (II) and alkyl palladium (II) complexes constitute an important class of such catalyst systems. With the right set of ligands, these complexes display activities that parallel those of the cationic systems. Currently, it is believed that polymerization using these catalyst systems involves disassociation of one of the ligands followed by coordination of the olefin that then inserts into a metal-carbon bond.

Another set of neutral complexes that display catalytic activity in the polymerization of olefins are chromium alkyl complexes. Pentamethyl cyclopentadienide chromium dialkyl complexes of the type, $Cp^*CrR_2$ wherein $Cp^*=C_5(CH_3)_5$, $R=CH_2Ph$ or $CH_2Si(CM_3)_3$ will readily polymerize various olefins. It is important to note that in these systems catalytic properties are only observed with bulky R groups. Presumably, the bulk of the R group prevents the formation of alkyl bridged dimers thereby insuring the existence of a coordinatively unsaturated chromium center. Such catalysts possess two metal alkyl bonds in which the olefin can insert and do not constitute single site catalysts. Preparation of the latter has been achieved by the use of amido ligand tethered to a cyclopentadienyl. These resulting complexes that have been characterized by X-ray analysis feature remarkable activities in the polymerization of various olefins.

SUMMARY OF THE INVENTION

In one aspect, the present invention is directed to a composition of matter for the polymerization or oligomerization of alpha olefins, the composition comprising a compound of the general formula:

$$[CpM(Ar_F)Y]_p \qquad (V)$$

wherein

Cp is a substituted or unsubstituted cyclopentadienyl ligand or cyclopentadienyl-type bulky ligand characterized by one or more open, acylic or fused ring systems comprised of atoms selected from Groups 13–16 of the Periodic Table of Elements and wherein the ligands can include a heteroatom;

M is a transition metal selected from Groups 3–9 of the Periodic Table of Elements;

$Ar_F$ is a fluorinated aryl group;

Y is a hydrocarbyl group that can contain a heteroatom; and p is 1 or 2.

Another preferred embodiment of the present invention involves the preparation of the catalyst compound having Formula V. The preferred method comprises reacting a first organometallic compound (hereinafter described as Formula I) with a first metal complex (hereinafter described as Formula II) to form a second, neutral metal complex (hereinafter described as Formula III) and reacting the neutral metal complex with a second organometallic compound (hereinafter described as Formula IV) to produce the catalyst compound (Formula V).

In yet another preferred embodiment of the present invention there is provided a process for the polymerization or oligomerization of an alpha olefin wherein at least one alpha olefin having from 2–20 carbon atoms is reacted in a catalytic system comprising the catalyst compound of Formula V in an inert solvent.

BRIEF DESCRIPTION OF THE DRAWINGS

FIG. 2 is a 3-dimensional depiction of the compound hereinafter identified as 2a; and FIG. 3 is a 3-dimensional depiction of the compound hereinafter identified as 3a.

DESCRIPTION OF THE PREFERRED EMBODIMENTS

Figure 1:
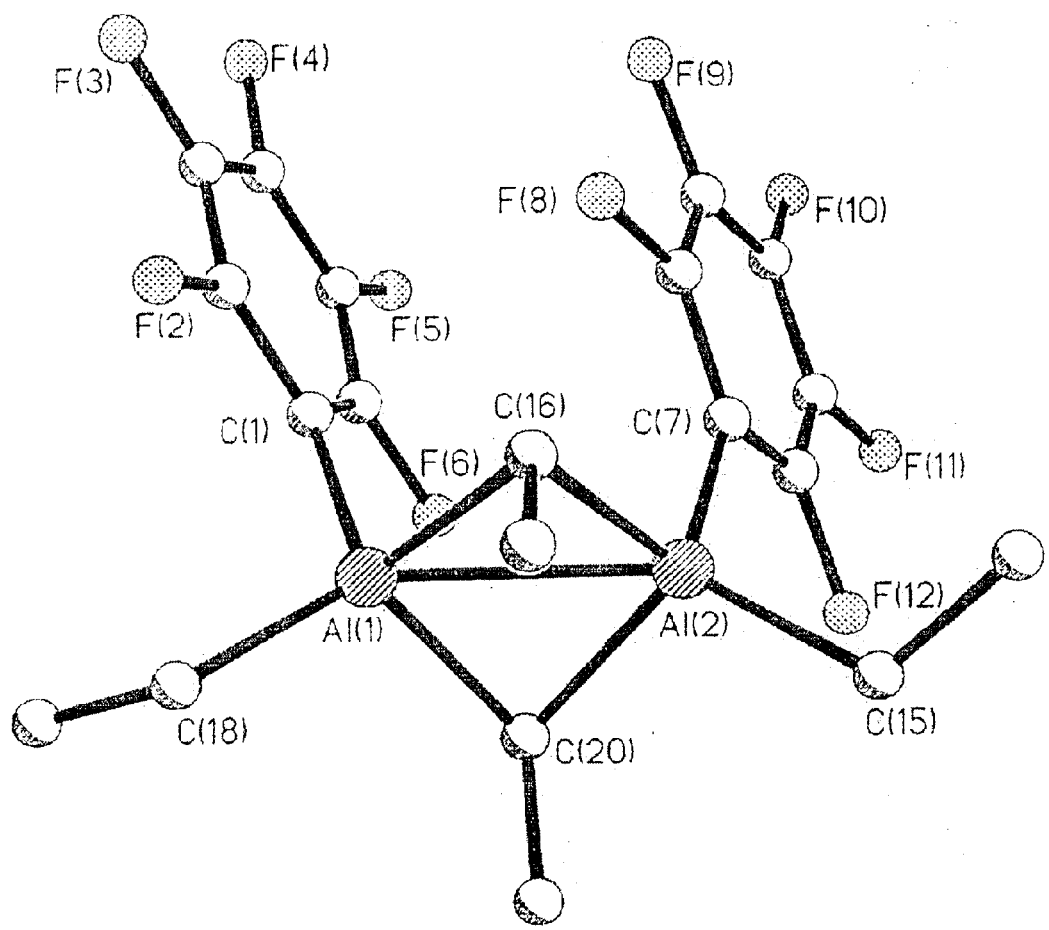
FIG. 1 is a 3-dimensional depiction of the compound hereinafter identified as 1b.

As will be seen hereafter, the catalyst compound (Formula V) of the present invention is formed from two well-defined components—the first component being a neutral metal complex, hereinafter described, the second component being an organometallic compound, hereinafter described.

The catalyst compound of the present invention has the general formula:

$$[CpM(Ar_F)Y]_p \qquad (V)$$

wherein

Cp is a substituted or unsubstituted cyclopentadienyl ligand or cyclopentadienyl-type bulky ligand characterized by one or more open, acylic or fused ring systems comprised of atoms selected from Groups 13–16 of the Periodic Table of Elements and wherein the ligands can include a heteroatom;

M is a transition metal selected from Groups 3–9 of the Periodic Table of Elements;

$Ar_F$ is a fluorinated aryl compound;

Y is a hydrocarbyl group that can contain a heteroatom; and p is 1 or 2.

The catalyst compound of the present invention includes a bulky ligand metallocene catalyst that, as described in U.S. Pat. No. 6,552,137 incorporated herein by reference for all purposes, include both half and full sandwich compounds having one or more bulky ligands bonded to at least one metal atom. The bulky ligand metallocene compounds preferred include one unsubstituted or substituted, cyclopentadienyl ligand or cyclopentadienyl-type ligand. These types of bulky ligand metallocene compounds are also referred to as half-sandwich compounds or mono-cyclopentadienyl compounds and the terms are used interchangeably herein. As noted, the unsubstituted or substituted cyclopentadienyl ligand or cyclopentadienyl-type bulky ligand is generally represented by one or more open, acyclic, or fused ring system typically composed of atoms selected from Groups 13–16 of the Periodic Table of Elements. Preferably, the atoms are selected from the group consisting of carbon, nitrogen, oxygen, silicon, sulphur, phosphorus, germanium, boron and aluminum or a combination thereof. The substituted or unsubstituted, cyclopentadienyl ligands or cyclopentadienyl-type ligands include heteroatom substituted and/or heteroatom containing cyclopentadienyl-type ligands.

Non-limiting examples of the bulky ligands include cyclopentadienyl ligands, as well as ligands selected from the group consisting of cyclopentaphenanthreneyl ligands, indenyl ligands, benzindenyl ligands, fluorenyl ligands, octahydrofluorenyl ligands, cyclooctatetraendiyl ligands, cyclopentacyclododecene ligands, azenyl ligands, azulene ligands, pentalene ligands, phosphoyl ligands, phosphinimine pyrrolyl ligands, pyrozolyl ligands, carbazolyl ligands, borabenzene ligands, hydrogenated versions thereof and mixtures thereof.

Bulky ligands that comprise one or more heteroatoms include those ligands containing nitrogen, silicon, boron, germanium, sulphur and phosphorus in combination with carbon atoms to form an open, acyclic, or preferably a fused, ring or ring system such as, for example, a hetero cyclopentadienyl ancillary ligand.

As noted, M is a metal selected from Groups 3–9 of the Periodic Table of Elements and is preferably a transition metal selected from Groups 3–6 of the Periodic Table of Elements. In an especially preferred embodiment, M is a transition metal selected from Groups 3–6 in the +3 oxidation state, Cr+3 being especially preferred.

As noted, $Ar_F$ is a fluorinated aryl group and can include pentafluorophenyl; 1,2perfluorobiphenyl; β-perfluoronapthyl; 2,4,6-tris(trifluoromethyl)phenyl; 3,5-bis(trifluoromethyl)phenyl and mixtures thereof. It will be understood that other fluorinated aryl compounds can be employed.

The Y group, as noted, is a hydrocarbyl group that can contain a heteroatom. Non-limiting examples of substituent groups Y include one or more from the groups selected from linear or branched alkyl radicals, alkenyl radicals, alkynyl radicals, cycloalkyl radicals, aryl radicals, acyl radicals, aroyl radicals, alkoxy radicals, aryloxy radicals, alkythio radicals, dialkylamino radicals, alkoxycarbonyl radicals, aryloxycarbonyl radicals, carbomoyl radicals, alkyl-or alkyl-carbamoyl radicals, acyloxy radicals, acylamino radicals, aroylamino radicals, straight, branched or cyclic, alkyline radicals or combinations thereof. In a preferred embodiment, the substituent group Y can have up to 50 non-hydrogen, primarily carbon atoms, that can also be substituted with halogen or the like. Preferred hydrocarbyl groups are those selected from the group consisting of (a) alkyl groups containing from 1 to 30 carbon atoms, (b) cycloalkyl groups containing from 3 to 12 carbon atoms, (c) substituted cycloalkyl groups wherein the cycloalkyl group contains from 3 to 12 carbon atoms and the substituent contains from 1 to 30 carbon atoms, (d) aryl groups containing from 6 to 30 carbon atoms, (e) any of groups (a–d) containing a heteroatom and (f) mixtures thereof. The heteroatoms can include sulphur, nitrogen, etc.

To prepare the catalyst compound of the present invention, a first, organometallic compound having the formula:

$$(Ar_F)_n EY_m D_o \quad (I)$$

wherein

D is selected from the group consisting of $Li^+$, $Na^+$, $K^+$, $Rb^+$, $Cs^+$, $[Y_4N]^+$, $[(C_6H_5)_3C]^+$, a pyridinium moiety and mixtures thereof.

E can be:

Li wherein n=1 and m=0 and o=0;
Na wherein n=1 and m=0 and o=0;
Mg wherein n=2 and m=0 and o=0;
Mg wherein n=1 and m=1 and o=0;
MgCl wherein n=1 and m=0 and o=0;
Mg Br wherein n=1 and m=0 and o=0;
B wherein n=3 and m=0 and o=0;
B wherein n=2 and m=1 and o=0;
B wherein n=1 and m=2 and o=0;
Al wherein n=3 and m=0 and o=0;
Al wherein n=2 and m=1 and o=0;
Al wherein n=1 and m=2 and o=0;
Ga wherein n=3 and m=0 and o=0;
Ga wherein n=2 and m=1 and o=0;
Ga wherein n=1 and m=2 and o=0;
In wherein n=3 and m=0 and o=0;
In wherein n=2 and m=1 and o=0;
In wherein n=1 and m=2 and o=0;
B wherein n=4 and m=0 and o=1;
B wherein n=3 and m=1 and o=1;
B wherein n=2 and m=2 and o=1;
B wherein n=1 and m=3 and o=1;
Al wherein n=4 and m=0 and o=1;
Al wherein n=3 and m=1 and o=1;
Al wherein n=2 and m=2 and o=1;
Al wherein n=1 and m=3 and o=1;
Ga wherein n=4 and m=0 and o=1;
Ga wherein n=3 and m=1 and o=1;
Ga wherein n=2 and m=2 and o=1;
Ga wherein n=1 and m=3 and o=1;
In wherein n=4 and m=0 and o=1;
In wherein n=3 and m=1 and o=1;
In wherein n=2 and m=2 and o=1;
In wherein n=1 and m=3 and o=1.

is reacted with a metal complex having the general formula:

$$[CpMX_2]_2 \quad (II)$$

wherein

X is F, Cl, Br, I or a mixture thereof.

to form a metal complex of the general formula:

$$[CpM(Ar_F)X]_2 \quad (III)$$

The complex of Formula III is then reacted with a second organometallic compound having the general formula:

$$AY_k \quad (IV)$$

wherein

A can be:
Li and k=1;
Na and k=1;
K and k=1;
Mg and k=2;
MgCl and k=1;
MgBr and k=1;
Al and k=3;
Ga and k=3;
In and k=3.

to produce the catalyst compound (Formula V).

The first organometallic compound (Formula I) can be prepared by well known methods such as by reacting a fluorinated aryl compound with a metal alkyl in a suitable inert solution and separating the first organometallic compound from the reaction mixture. For example, a fluorinated aryl compound such as boron tripentafluorophenyl can be reacted with a trialkyl aluminum compound in an inert organic solvent such as pentane, hexane, benzene, etc. The resulting product will have a structure corresponding to Formula I depending upon the nature of E and D. Although the compounds depicted by Formula I are shown as "monomeric," it is to be understood that compounds having Formula I exist as dimers, trimers and the other oligimers, those various species being in equilibrium. A preferred form of the organometallic compound having Formula I is one wherein $Ar_F$ is pentaflurolphenyl, E is aluminum, Y is a lower alkyl, e.g., methyl, ethyl and m is 2 and n is 1.

Although metal complexes having the Formula II can be purchased, they can also be conveniently made by the following general process: A stirred suspension of a transition metal halide/tetrahydrofuran (THF) complex can be admixed in equal molar quantities with an alkali metal pentamethylcyclopentadieneide. Thus, in a specific example, a stirred suspension of a chromium chloride/tetahydrofuran complex in toluene, tetahydrofuran or some similar solvent is added in equal molar quantities to lithium pentamethylcyclopentadieneide with stirring. This reaction produces bis[($\eta^5$-pentamethylcyclopentadienyl)(chloro)($\mu$-chloro)chromium(III)]. The product can be purified by filtration or recrystallization and in certain cases can be used without removal of the byproduct, e.g., the alkali metal halide salt, e.g., lithium chloride.

To produce the neutral metal complex having the Formula III, and as noted above, the organometallic compound having the Formula I is reacted with the metal complex having the Formula II. This is generally conducted in an inert solution such as pentane, hexane, benzene, toluene, etc. at room temperature and in an inert atmosphere. The product, i.e., the neutral metal complex having the Formula III is generally recovered by removing the solvent using vacuum followed by redesolving of the residue in toluene or the like and filtering.

After the neutral metal complex having the Formula III has been formed, it is reacted with a second organometallic compound having the general Formula IV, the reaction, again, being conveniently carried out in a solvent such as THF. In this regard, the neutral metal complex of Formula III dissolved in THF is admixed with the second organometallic compound having the Formula IV, e.g., lithium methyl, dissolved in a solvent such as ether, the reaction being carried out at room temperature and in an inert atmosphere.

The catalysts of the present invention can be used to polymerize or oligomerize alpha olefins such as ethylene by a general procedure wherein the alpha olefin, e.g., ethylene is introduced into a solution of the catalysts for a desired period of time until the desired degree of polymerization has been achieved. The catalysts of the present invention can also be used to oligomerize alpha olefins such as ethylene by a general procedure wherein the alpha olefin, e.g., ethylene is introduced into a solution of the catalyst and a trialkylaluminum such as triethyl aluminum for a desired period of time until the desired degree of oligomerization has been achieved. Virtually any alpha olefin can be employed, alpha olefins containing from 2 to 20, especially from 2 to 8, carbon atoms being particularly preferred.

To more fully illustrate the present invention, the following non-limiting examples are presented. In all cases, the reactions were performed in an inert atmosphere using standard glove box and vacuum-line techniques.

EXAMPLE 1

Synthesis of $[Al(CH_3)_2(C_6F_5)]_2$ 1a

To a hexane (20mL) solution of $B(C_6F_5)_3$ (0.200 g. 0.39 mmol) was added $Al(CH_3)_3$ (0.085 g, 1.18 mmol). The mixture was stirred for about 1 h. The solvent and $B(CH_3)_3$ were removed under vacuum to give a white solid $[Al(CH_3)_2 C_6F_5)]_2$, compound 1a (0.253 g, 1.13 mmol, 96%). This compound was crystallized from hexane at $-20°$ C.

EXAMPLE 2

Synthesis of $[AlEt_2(C_6F_5)]_2$ 1b

To a hexane (20 mL) solution of $B(C_6F_5)_3$ (0.200 g, 0.39 mmol) was added $Al(C_2H_5)_3$ (0.134 g, 1.17 mmol). The mixture was stirred for about 1 h. The solvent and $B(C_2H_5)_3$ were removed under vacuum to give a white solid $[Al(C_2H_5)_2(C_6F_5)]_2$, compound 1b (0.279 g, 1.10 mmol, 95%). This compound was crystallized from hexane at $-20°$ C. Elemental, X-ray crystallographic and NMR analyses confirmed the structure of the compound 1b. The structure of compound 1b is depicted in FIG. 1.

EXAMPLE 3

Synthesis of $[Cp*CrCl(C_6F_5)]_2$ 2a

Figure 2:
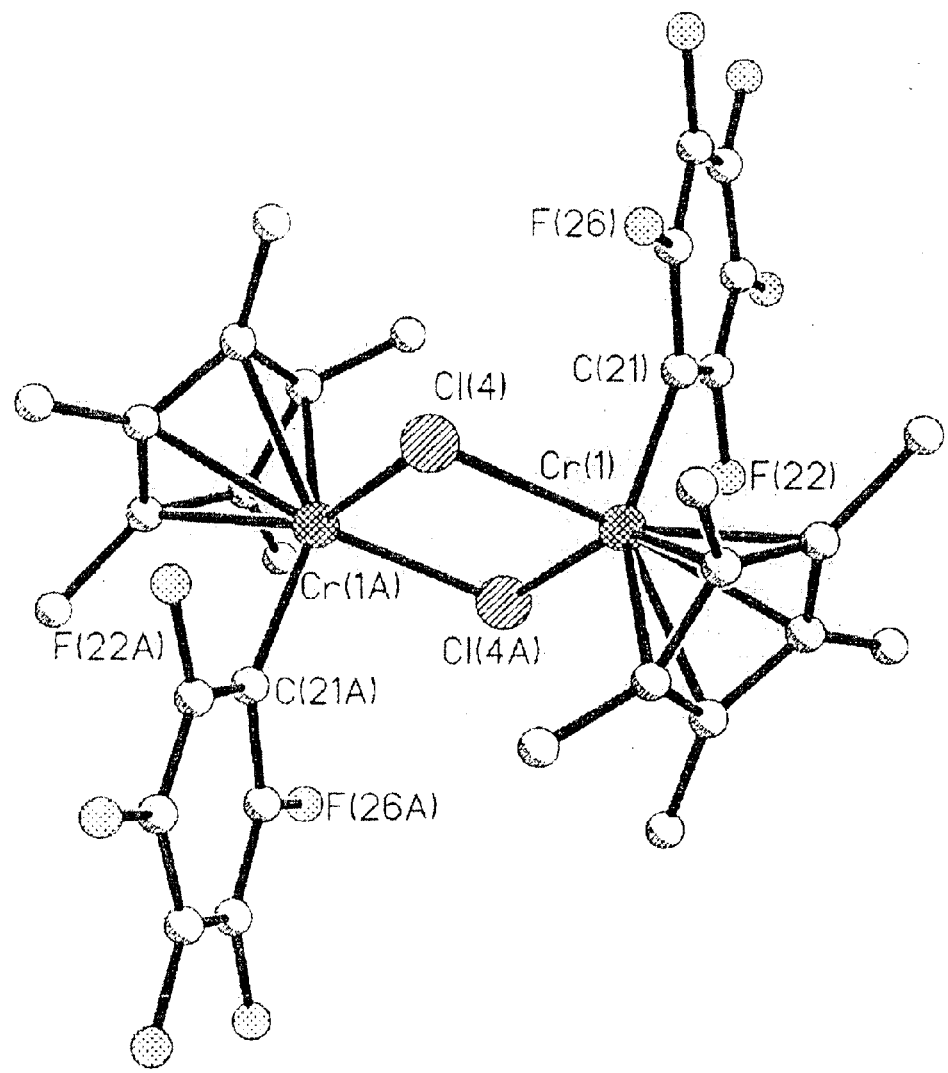

To a toluene solution of $[Cp*CrCl_2]_2$ (0.200 g, 0.39 mmol) was added $[Al(CH_3)_2(C_6F_5)]_2$ (0.174 g, 0.39 mmol). The color of the solution turned from greenish blue to dark blue immediately. After the solution was allowed to stir for about 3 days, the solvent was evaporated by vacuum to dryness. The resulting residue was re-dissolved in toluene (20 mL) and filtered. Dark blue crystals of compound 2a (0.094 g, 24%) were obtained from this solution upon layering with hexane at room temperature for 5 days. Elemental, X-ray crystallographic and NMR analyses confirmed the structure of compound 2a. The structure of compound 2a is depicted in FIG. 2.

EXAMPLE 4

Synthesis of $[Cp*Cr(CH_3)(C_6F_5)]_2$ 3a

Figure 3:
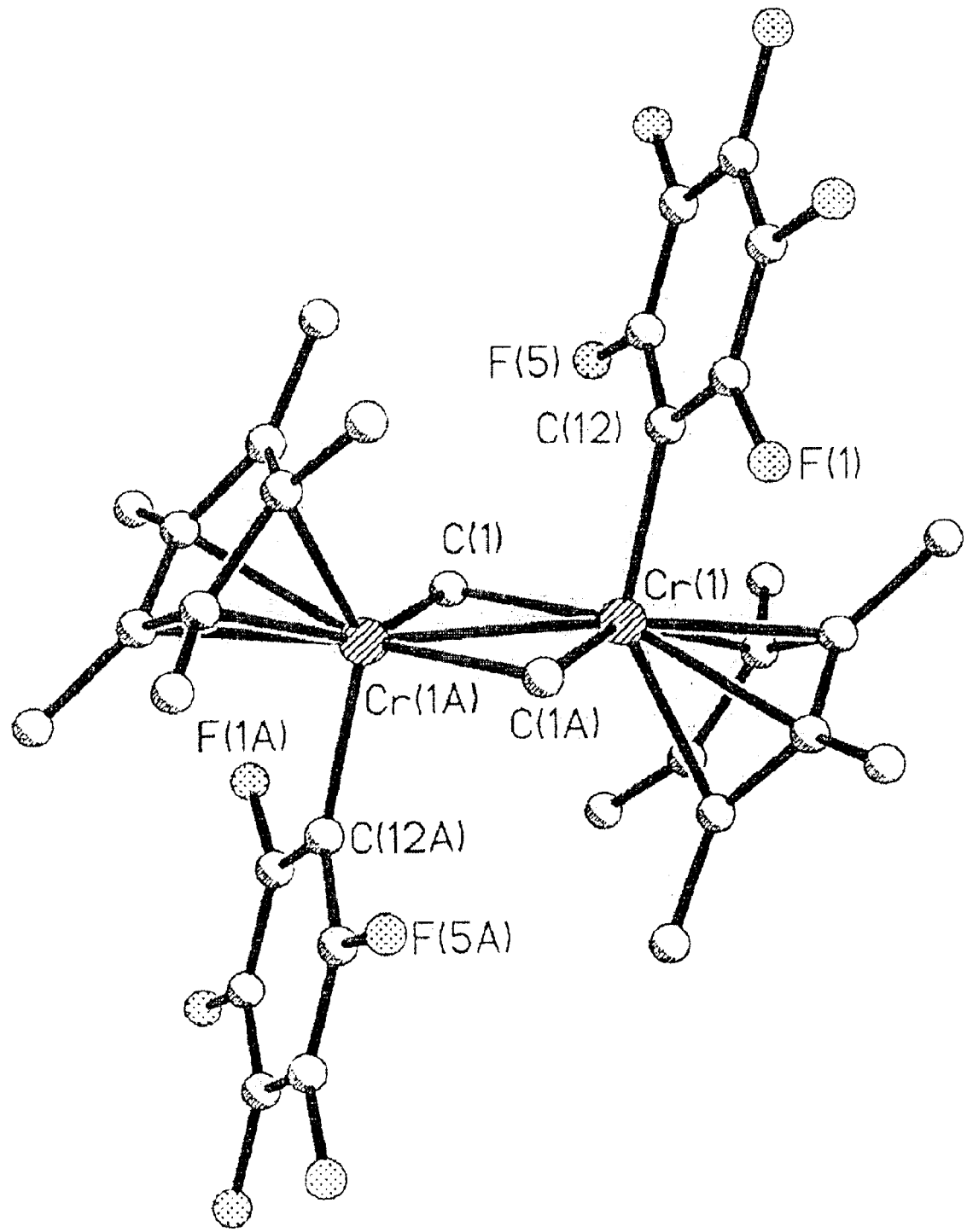

Compound 2a (0.200 g, 0.39 mmol) was generated in situ by the above method. The toluene solvent was removed and the resulting residue was dissolved in THF (20 mL). To this solution $CH_3$ Li (1.56 mmol, 1 mL, 1.6M in ether) was added. The color of the solution turned from dark blue to dark purple. After stirring for 10 min. the solvent was removed and the resulting residue was dissolved in hexane and filtered. The hexane solution was concentrated to 10 mL. Dark red crystals of 3a (0.120 g, 42%) were obtained from this hexane solution at $-20°$ C. for 2 days. Elemental, NMR and X-ray crystallographic analyses confirmed the structure of compound 3a. The structure of compound 3a is depicted in FIG. 3.

EXAMPLE 5
Ethylene Polymerization and Oligomerization

A toluene (30 mL) solution of $[Cp^*Cr(CH_3)(C_6F_5)]_2$ (0.010 g, 0.024 mmol) was mixed with $Al(C_2H_5)_3$ (0.139 g, 1.22 mmol) in a 200 mL Schlenk flask. The aluminum triethyl was added to promote the oligomerization of ethylene to produce alkanes (Cy-$C_{30}$). The color of the solution turned from purple to dark brown. The solution was exposed to an atmosphere of ethylene which resulted in an exothermic reaction. After approximately 30 minutes, polyethylene started to precipitate. The reaction was allowed to continue for one hour, after which the ethylene feed was discontinued. The white polyethylene precipitate was isolated by filtration and washed with acetone. The filtrate was quenched by slow addition of 10 mL of water at room temperature. The toluene fraction was separated and the solvent was removed under vacuum to give an oily residue which was analyzed by gas chromatography (GC) and mass spectrometry (MS).

The GC/MS spectrum showed that the oily residue consisted of a mixture of shorter alkanes ($C_{10}$–$C_{22}$) of even-carbon numbers. It is interesting to note that, using the present invention, oligomerization of ethylene is produced by a neutral Cr(III) alkyl complex in contrast to the reports regarding prior art cationic Cr(III) alkyl complexes.

As can be seen from the above data, the catalysts of the present invention are neutral and do not require activators such as methylalumoxane as is the case with certain cationic catalysts. The catalysts of the present invention are single site in the sense that they possess a single site for olefin insertion. Furthermore, as is well known, transfer of a fluorinated aryl group to the transition metal center of a catalyst of the general type under consideration usually leads to loss of catalytic activity. However, with the present catalyst no such loss in activity is observed. The catalysts of the present invention are unique in being the first neutral catalysts bearing a cyclopentadienyl ligand, a fluorinated aryl group and an alkyl group bound to a transition metal center, the transition metal being in the +3 oxidation state. As is also observed from above, in the presence of a metal alkyl such as trialkyl aluminum the catalysts of the present invention are able to promote the oligomerization of olefins to produce short alkane alkyls in the $C_4$–$C_{30}$ range, the alkyls being even carbon numbered.

The foregoing description and examples illustrate selected embodiments of the present invention. In light thereof, variations and modifications will be suggested to one skilled in the art, all of which are in the spirit and purview of this invention.

What is claimed is:

1. A composition of matter comprising a compound having the general formula:

$$[CpM(Ar_F)Y]_p$$

wherein
Cp is a substituted or unsubstituted cyclopentadienyl ligand or cyclopentadienyl-type bulky ligand characterized by one or more open, acylic or fused ring systems comprised of atoms selected from Groups 13–16 of the Periodic Table of Elements and wherein the ligands can include a heteroatom;
M is a metal selected from Groups 3–9 of the Periodic Table of Elements;
$Ar_F$ is a fluorinated aryl group;
Y is a hydrocarbyl group that can contain a heteroatom; and
p is 1 or 2.

2. The composition of claim 1 wherein Cp is a cyclopentadienyl ligand.

3. The composition of claim 1 wherein Cp is pentamethylcyclopentadienyl ligand.

4. The composition of claim 1 wherein Y is selected from the group consisting of (a) alkyl groups containing from 1 to 30 carbon atoms, (b) cycloalkyl groups containing from 3 to 12 carbon atoms, (c) substituted cycloalkyl groups wherein the cycloalkyl group contains from 3 to 12 carbon atoms and the substituent contains from 1 to 30 carbon atoms, (d) aryl groups containing from 6 to 30 carbon atoms, (e) any of groups (a–d) containing a heteroatom and (f) mixtures thereof.

5. The composition of claim 1 wherein Cp is selected from the group consisting of cyclopentaphenanthreneyl ligands, indenyl ligands, benzindenyl ligands, fluorenyl ligands, octahydrofluorenyl ligands, cyclooctatetraendiyl ligands, cyclopentacyclododecene ligands, azenyl ligands, azulene ligands, pentalene ligands, phosphoyl ligands, phosphinimine pyrrolyl ligands, pyrozolyl ligands, carbazolyl ligands, borabenzene ligands, hydrogenated versions thereof and mixtures thereof.

6. The composition of claim 4 wherein Y is a methyl group.

7. The composition of claim 1 wherein $Ar_F$ is selected from the group consisting of pentafluorophenyl; 1,2 perfluorobiphenyl; β-perfluoronapthyl; 2,4,6-tris(trifluoromethyl)phenyl; 3,5-bis(trifluoromethyl)phenyl and mixtures thereof.

8. The composition of claim 7 wherein $AR_F$ is a $C_6F_5$ group.

9. The composition of claim 1 wherein M is $Cr^{+3}$.

10. A method of preparing a catalyst composition comprising:

reacting a first organometallic compound having the formula:

$$(Ar_F)_n EY_m D_o \qquad (I)$$

wherein
$Ar_F$ is a fluorinated aryl group;
D is selected from the group consisting of $Li^+$, $Na^+$, $K^+$, $Rb^+$, $Cs^+$, $[Y_4N]^+$, $[(C_6H_5)_3C]^+$, a pyridinium moiety and mixtures thereof;
E can be:
Li wherein n=1 and m=0 and o=0;
Na wherein n=1 and m=0 and o=0;
Mg wherein n=2 and m=0 and o=0;
Mg wherein n=1 and m=1 and o=0;
MgCl wherein n=1 and m=0 and o=0;
MgBr wherein n=1 and m=0 and o=0;
B wherein n=3 and m=0 and o=0;
B wherein n=2 and m=1 and o=0;
B wherein n=1 and m=2 and o=0;
Al wherein n=3 and m=0 and o=0;
Al wherein n=2 and m=1 and o=0;
Al wherein n=1 and m=2 and o=0;
Ga wherein n=3 and m=0 and o=0;
Ga wherein n=2 and m=1 and o=0;
Ga wherein n=1 and m=2 and o=0;
In wherein n=3 and m=0 and o=0;
In wherein n=2 and m=1 and o=0;
In wherein n=1 and m=2 and o=0;
B wherein n=4 and m=0 and o=1;
B wherein n=3 and m=1 and o=1;
B wherein n=2 and m=2 and o=1;
B wherein n=1 and m=3 and o=1;

Al wherein n=4 and m=0 and o=1;
Al wherein n=3 and m=1 and o=1;
Al wherein n=2 and m=2 and o=1;
Al wherein n=1 and m=3 and o=1;
Ga wherein n=4 and m=0 and o=1;
Ga wherein n=3 and m=1 and o=1;
Ga wherein n=2 and m=2 and o=1;
Ga wherein n=1 and m=3 and o=1;
In wherein n=4 and m=0 and o=1;
In wherein n=3 and m=1 and o=1;
In wherein n=2 and m=2 and o=1;
In wherein n=2 and m=3 and o=1;

Y is a hydrocarbyl group that can contain a heteroatom, with a metal complex having the general formula:

$$[CpMX_2]_2 \quad (II)$$

wherein
X is F, Cl, Br, I or a mixture thereof;
M is a transition metal selected from Groups 3–9 of the Periodic Table of Elements;
Cp is a substituted or unsubstituted cyclopentadienyl ligand or cyclopentadienyl-type bulky ligand characterized by one or more open, acylic or fused ring systems comprised of atoms selected from Groups 13–16 of the Periodic Table of Elements and wherein the ligands can include a heteroatom, to form a neutral metal complex of the general formula:

$$[CpM(Ar_F)X]_2; \quad (III)$$

reacting the complex of Formula III with a second organometallic compound having the general formula:

$$AY_k \quad (IV)$$

wherein
A can be:
Li and k=1;
Na and k=1;
K and k=1;
Mg and k=2;
MgCl and k=1;
MgBr and k=1;
Al and k=3;
Ga and k=3;
In and k=3;

to produce a catalyst composition having the general formula:

$$[CpM(Ar_F)Y]_p \quad (V)$$

wherein
Cp is a substituted or unsubstituted cyclopentadienyl ligand or cyclopentadienyl-type bulky ligand characterized by one or more open, acylic or fused ring systems comprised of atoms selected from Groups 13–16 of the Periodic Table of Elements and wherein the ligands can include a heteroatom;
M is a metal selected from Groups 3–9 of the Periodic Table of Elements;
$Ar_F$ is a fluorinated aryl group;
Y is a hydrocarbyl group that can contain a heteroatom; and
p is 1 or 2.

11. The method of claim 10 wherein Y is selected from the group consisting of (a) alkyl groups containing from 1 to 30 carbon atoms, (b) cycloalkyl groups containing from 3 to 12 carbon atoms, (c) substituted cycloalkyl groups wherein the cycloalkyl group contains from 3 to 12 carbon atoms and the substituent contains from 1 to 30 carbon atoms, (d) aryl groups containing from 6 to 30 carbon atoms, (e) any of groups (a–d) containing a heteroatom and (f) mixtures thereof.

12. A process for the polymerization or oligomerization of an alpha olefin comprising introducing at least one alpha olefin having from 2 to 20 carbon atoms into a catalytic system comprising the catalytic composition of any of claims 1–8 and a trialkyl aluminum, an inert solvent.

13. A process of claim 12 wherein said alpha olefin is ethylene.

14. The process of claim 12 wherein said catalytic system comprises:

$$[CpCr(CH_3)(C_6F_5)]_2.$$

15. The process of claim 12 wherein said olefins have from 2 to 8 carbon atoms.

* * * * *